United States Patent
Yang et al.

(10) Patent No.: US 10,889,857 B2
(45) Date of Patent: Jan. 12, 2021

(54) METHOD TO FABRICATE A NANOCHANNEL FOR DNA SEQUENCING BASED ON NARROW TRENCH PATTERNING PROCESS

(71) Applicant: SEAGATE TECHNOLOGY LLC, Cupertino, CA (US)

(72) Inventors: Xiaomin Yang, Livermore, CA (US); ShuaiGang Xiao, Fremont, CA (US); David S. Kuo, Palo Alto, CA (US); Koichi Wago, Sunnyvale, CA (US); Thomas Young Chang, Menlo Park, CA (US)

(73) Assignee: SEAGATE TECHNOLOGY LLC, Fremont, CA (US)

( * ) Notice: Subject to any disclaimer, the term of this patent is extended or adjusted under 35 U.S.C. 154(b) by 249 days.

(21) Appl. No.: 15/886,533

(22) Filed: Feb. 1, 2018

(65) Prior Publication Data

US 2018/0216179 A1  Aug. 2, 2018

Related U.S. Application Data

(60) Provisional application No. 62/453,307, filed on Feb. 1, 2017.

(51) Int. Cl.
*C12Q 1/6869* (2018.01)
*B82Y 15/00* (2011.01)
*C12M 1/34* (2006.01)

(52) U.S. Cl.
CPC ............ *C12Q 1/6869* (2013.01); *C12M 1/34* (2013.01); *B82Y 15/00* (2013.01); *C12Q 2563/159* (2013.01)

(58) Field of Classification Search
None
See application file for complete search history.

(56) References Cited

U.S. PATENT DOCUMENTS 8,901,621 B1 * 12/2014 Bai .................. G01N 27/403
257/253
9,410,923 B2    8/2016 Sauer et al.
(Continued)

FOREIGN PATENT DOCUMENTS

WO   WO 2015/042200 A1 *  3/2015 ............. G01N 33/68

OTHER PUBLICATIONS

Di Ventra, Massimiliano, et al., "Decoding DNA, RNA and peptides with quantum tunneling," Nature Nanotechnology, vol. 11, Feb. 2016, pp. 117-126.
(Continued)

*Primary Examiner* — Robert T. Crow
(74) *Attorney, Agent, or Firm* — Holzer Patel Drennan

(57) ABSTRACT

Apparatus and methods relating to DNA sequencing are provided. In one embodiment, a DNA sequencing device includes a nanochannel having a width that is approximately 0.3 nm to approximately 20 nm. A pair of electrodes having portions exposed to the nanochannel may form a tunneling current electrode (TCE) with an electrode gap of approximately 0.1 nm to approximately 2 nm, and more particularly about 0.3 nm to about 1 nm. In one embodiment, at least one of the pair of electrodes is formed as a suspended electrode. An actuator may be associated with the suspended electrode to displace it relative to the other electrode. In various embodiments, the nanochannel and/or the electrodes may be formed using thermal reflow processes to reduce the size of such features.

19 Claims, 11 Drawing Sheets

(56) References Cited

U.S. PATENT DOCUMENTS

2009/0283412 A1* 11/2009 Sansinena ........ G01N 33/48721
   205/122
2011/0120868 A1* 5/2011 Lindsay ................. B82Y 15/00
   204/452
2013/0256013 A1* 10/2013 Sirman .................. B82Y 40/00
   174/257

OTHER PUBLICATIONS

Feng, Yanxiao, et al., "Nanopore-based Fourth-generation DNA Sequencing Technology," Genomics Proteomics Bioinformatics, 13 (2015), pp. 4-16.

Ivanov, A.P., et al., "DNA Tunneling Detector Embedded in a Nanopore," Nano Letters, 2011, 11, pp. 279-285.

Ke, Rongqin, et al., "Fourth Generation of Next-Generation Sequencing Technologies: Promise and Consequences," Human Mutation, vol. 37, No. 12, 2016, pp. 1363-1367.

Kulski, Jerzy K., "Next-Generation Sequencing—An Overview of the History, Tools, and 'Omic' Applications," http://dx.doi.org/10.5772/61964, 59 pages.

\* cited by examiner

METHOD TO FABRICATE A NANOCHANNEL FOR DNA SEQUENCING BASED ON NARROW TRENCH PATTERNING PROCESS

RELATED APPLICATIONS

This application claims the benefit of the filing date of U.S. Provisional Application No. 62/453,307, filed on 1 Feb. 2017, and entitled METHOD TO FABRICATE A NANOCHANNEL FOR DNA SEQUENCING BASED ON NARROW TRENCH PATTERNING PROCESS, the disclosure of which is incorporated in its entirety by this reference.

SUMMARY

One aspect of the present disclosure relates to a DNA sequencing device that includes a substrate, an in-plane nanochannel positioned in the substrate, the nanochannel having a width in the range of about 0.3 nm to about 20 nm, and a pair of in-plane electrodes positioned in the substrate and arranged perpendicular to the nanochannel. Free ends of the electrodes are exposed in the nanochannel and spaced apart to form an electrode gap. The electrode gap is in the range of about 0.3 nm to about 2 nm.

A height of the nanochannel may be in the range of about 5 nm to about 20 nm. The electrodes may have a width in the range of about 0.1 nm to about 20 nm. The electrodes may have a height in the range of about 5 nm to about 20 nm. The nanochannel may be formed in an insulator substrate. The nanochannel may include a metal layer positioned along a bottom surface, and the metal layer may be covered with an insulator material. The insulator substrate may include SiO2 or glass.

At least one of the electrodes may be formed as a suspended electrode. An actuator may be associated with the suspended electrode and configured to laterally displace the electrode, altering the width of the electrode gap.

Another aspect of the present disclosure relates to a method of forming a nanochannel device for DNA sequencing. The method includes depositing a hard mask layer on an insulator substrate, depositing a first resist layer on the hard mask layer, trench patterning the first resist layer to form a first trench, and shrinking the first trench using a thermal re-flow process. The method also include pattern transferring the first trench through the hard mask layer and into the insulator substrate, stripping the hard mask layer from the insulator substrate, filling the first trench with a fill material, trench patterning the insulator substrate to form an electrode trench, the electrode trench intersecting the first trench, depositing metal material in the electrode trench to form a pair of electrodes, and removing the fill material from the first trench to form a DNA nanochannel.

The method may include trench patterning using at least one of deep ultraviolet (DUV) lithography, 193 nm lithography, e-beam lithography, and nanoimprint lithography (NIL). The method may include repeating the step of shrinking the first trench until the first trench has a first trench width in the range of about 0.3 nm to about 20 nm. The pattern transferring may include reactive ion etching (RIE). The method may include, after pattern transferring, stripping the first resist layer from the hard mask layer. The method may include, after stripping the hard mask layer, depositing a metal layer on the insulator substrate as a capping layer, the metal layer positioned along a bottom surface of the first trench, etching to remove the metal layer from the insulator substrate except in the first trench, and depositing an insulator material in the first trench to cover the metal layer.

Filling the first trench with the filler material may include spin coating the filler material on the insulator substrate and in the first trench, and etching back the filler material from the insulator substrate except within the first trench. The method may include, after filling the first trench with the filler material, depositing a second resist layer on the insulator substrate, trench patterning the second resist layer to form a second trench, shrinking the second trench using the one or more thermal re-flow process, and trench patterning the insulator substrate to form the electrode trench using the second trench as a pattern.

The thermal re-flow process may include disposing a top coat over at least a portion of the substrate and within the trench. The top coat may include a water based solution with surfactants that have positively and negatively charged functional groups. The device, with the top coat, is baked for a prescribed time and at a prescribed temperature, and the top coat is then remove. The device may then be rinsed with deionized water, the resulting trench width having shrunk in the process while maintaining the cross-sectional profile or geometry of the trench. The method may also include baking the device with the top coat at a temperature of approximately 100° C. to approximately 180° C. for approximately 60 seconds to approximately 90 seconds, and removing the top coat from the substrate and the first trench.

The method may include, after depositing metal material in the electrode trench, etching back the metal material to expose the fill material. The method may include providing a base insulator layer on the substrate, wherein the first electrode layer is positioned on the base insulator layer. The electrodes may be spaced apart to form an electrode gap, the electrode gap may be positioned in the nanochannel, and the electrode gap may have a width in the range of about 0.3 nm to about 1 nm. The method may include applying an electrical voltage to the electrodes to narrow the electrode gap. A width of nanochannel may be in the range of about 0.3 nm to about 20 nm, and a height of the nanochannel may be in the range of about 5 nm to about 20 nm. The electrode may have a width in the range of about 0.1 nm to about 20 nm, and a height in the range of about 5 nm to about 20 nm.

Another aspect of the present disclosure relates to a method of sequencing DNA. The method includes providing a DNA sequencing device having a substrate, a nanochannel extending through a portion of the substrate, the nanochannel having a width in the range of about 0.3 nm to about 20 nm, and a pair of in-plane electrodes positioned in the substrate and arranged substantially perpendicular to the nanochannel, a portion of each electrode being exposed in the nanochannel to form an electrode gap, the electrode gap being in the range of about 0.3 nm to about 2 nm. The method further includes passing a DNA strand through the electrode gap, detecting a change in electronic signal with the electrodes as the DNA strand passes through the electrode gap, and determining a sequence of individual nucleotides of the DNA strand based on the change in electronic signal.

The foregoing has outlined rather broadly the features and technical advantages of examples according to this disclosure so that the following detailed description may be better understood. Additional features and advantages will be described below. The conception and specific examples disclosed may be readily utilized as a basis for modifying or designing other structures for carrying out the same purposes of the present disclosure. Such equivalent constructions do not depart from the scope of the appended claims.

Characteristics of the concepts disclosed herein, including their organization and method of operation, together with associated advantages will be better understood from the following description when considered in connection with the accompanying figures. Each of the figures is provided for the purpose of illustration and description only, and not as a definition of the limits of the claims.

BRIEF DESCRIPTION OF THE DRAWINGS

A further understanding of the nature and advantages of the present disclosure may be realized by reference to the following drawings. In the appended figures, similar components or features may have the same reference label. Further, various components of the same type may be distinguished by following a first reference label with a dash and a second label that may distinguish among the similar components. However, features discussed for various components, including those having a dash and a second reference label, apply to other similar components. If only the first reference label is used in the specification, the description is applicable to any one of the similar components having the same first reference label irrespective of the second reference label.

DETAILED DESCRIPTION

Figure 1A:
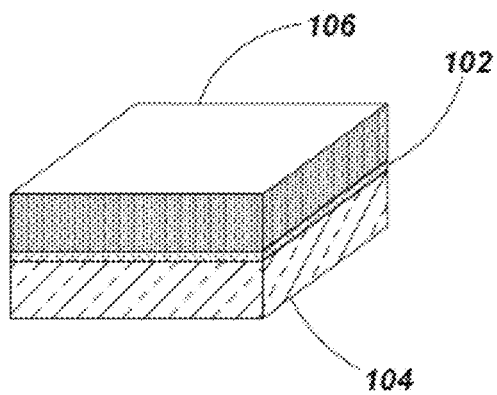
FIGS. 1A-1N illustrate fabrication steps for forming a DNA nanochannel device in accordance with an embodiment of the present disclosure.

Despite considerable efforts, DNA sequencing today still suffers from high costs and low speeds. To address all these issues, various methods have been proposed over the past decade that would allow individual DNA strands to be read directly. Among these, nanopore and nanochannel based approaches have emerged as the most promising. However, many challenges exist related to fabricating a channel and/or pore opening that is sufficiently small to limit passage to a single DNA strand, and there is no such report of a relatively mature method that address this unmet need.

Direct DNA sequencing has drawn attention due to its advantages on long read length, high throughput and low cost. Direct DNA sequencing methods using transverse tunneling current measurement have been studied extensively in literature. However, a manufacturably viable direct DNA sequencing device with required dimensions for the gap between the nanoelectrodes, nor methods for creating such a device, have not been discovered. Conventional MEMS and nanofabrication methods are inadequate for creating the required structure.

The present disclosure generally relates to DNA sequencing, and more particularly relates to DNA sequencing devices having nanochannels and nanoelectrodes, and related methods of fabricating such devices. The present disclosure may also relate to DNA sequencing using such devices.

A method of fabricating a nanochannel in a DNA sequencing device with dimensions as small as a few nanometers is disclosed here. One feature of the device is the relative long, narrow nanochannel for guiding the single molecule DNA to flow through. Another feature of the device is a tunneling current electrode (TCE) having a narrowing gap between the electrode members of the TCE. The TCE gap is required to be as small as 1 nm, or even smaller, in order to detect DNA signals at desired levels. The devices and methods disclosed herein may incorporate a two-stage narrow trench patterning process and may include a step of rotation of about 90°. An advantage of using a trench patterning process instead of an isolated line in the device provides the advantage of the trench limiting, if not avoiding, thin line pattern collapse issues associated with the formation of an isolated line.

A relatively fast and low-cost genome (DNA), transcriptome (RNA) and proteome (all proteins) sequencing method could lead to the development of personalized medicine (e.g., the ability to target drugs and medical treatments specially to an individual). However, fabrication of a nanochannel for single molecular DNA sequencing is still a technical challenge due to the extremely small dimension involved with the devices that are used to conduct the sequencing. The devices and methods disclosed herein address at least some of these challenges.

As discussed above, the device and methods disclosed herein provide a relatively long and narrow channel for guiding the single molecule DNA to flow through the device, and an even narrower tunneling current electrode (TCE). The TCE gap is required to be as small as less than about 1 nm in order to detect the DNA signal at a desired level. To reduce the TCE gap to less than about 1 nm, one TCE electrode member is formed as a suspended electrode, and a shear actuator is used at this electrode, as will be discussed in further detail below. In the production of the device, a thermal re-flow process may be used to produce trenches with a reduced gap between adjacent vertical sidewalls.

Figure 1B:
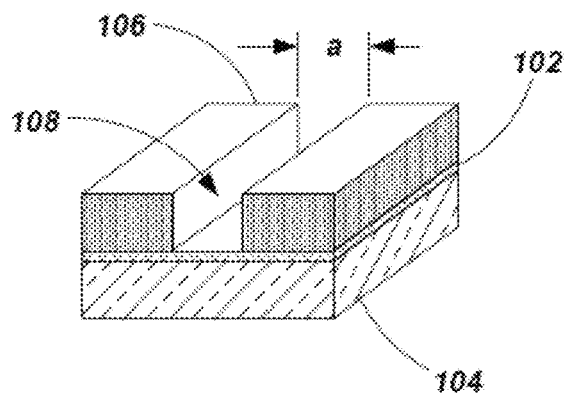
Figure 1C:
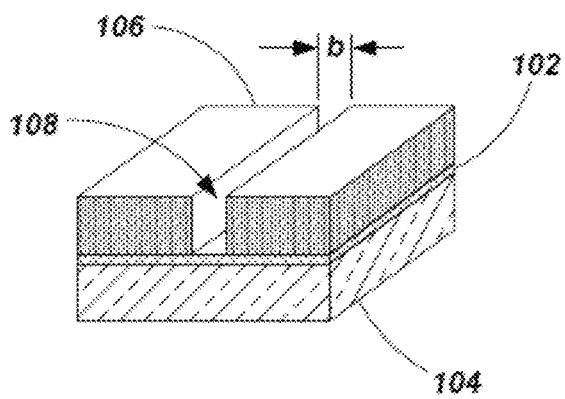
Figure 1D:
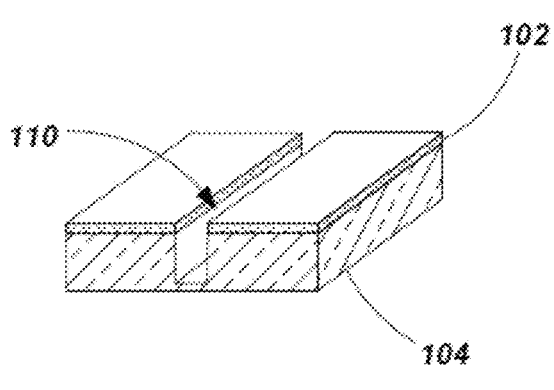
Figure 1E:
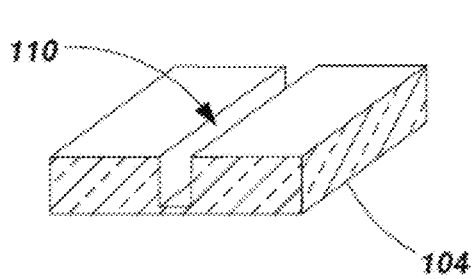
Figure 1F:
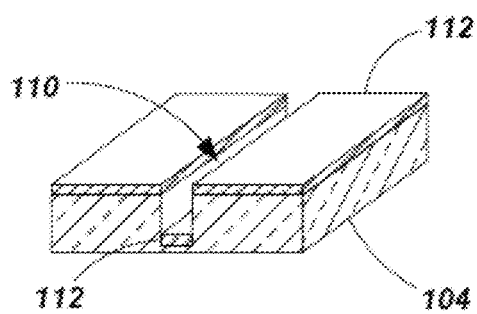
Figure 1G:
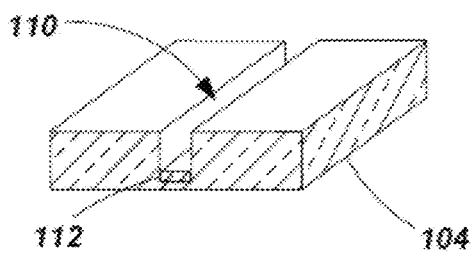
Figure 1H:
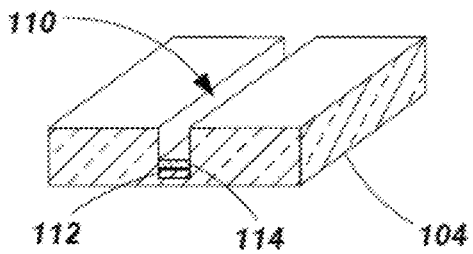
Figure 1I:
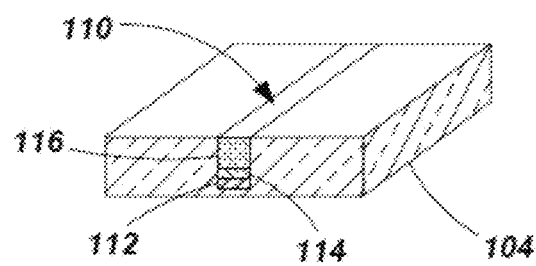
Figure 1J:
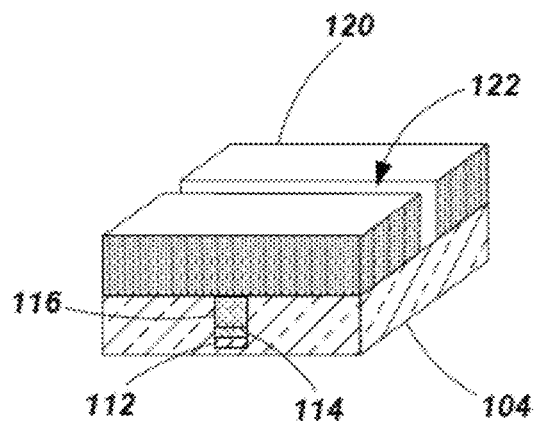
Figure 1K:
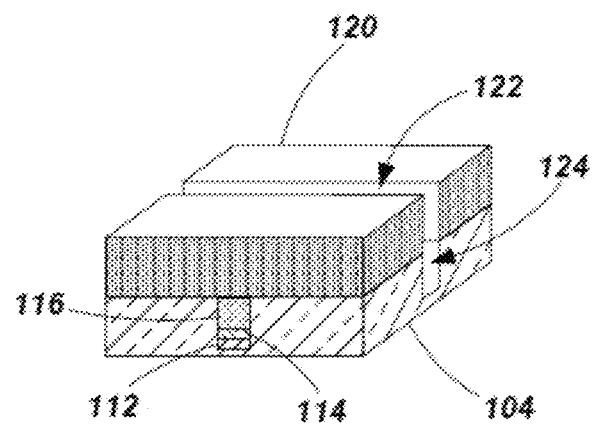
Figure 1L:
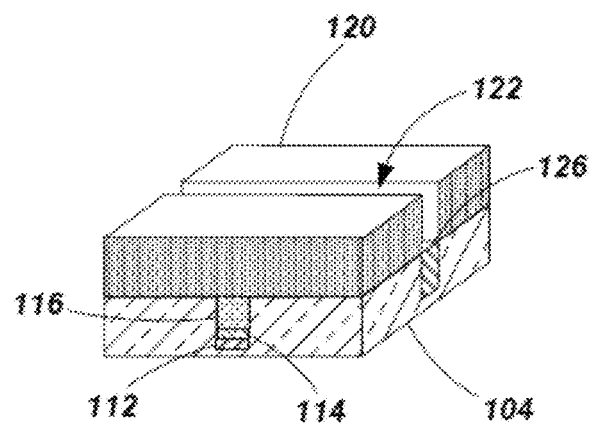
Figure 1M:
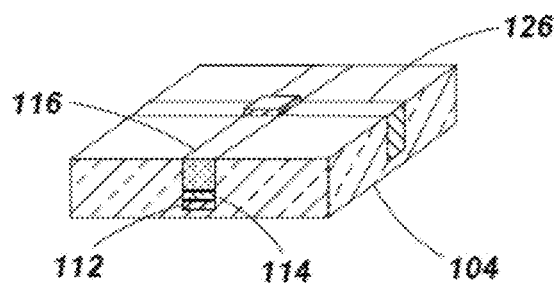
Figure 1N:
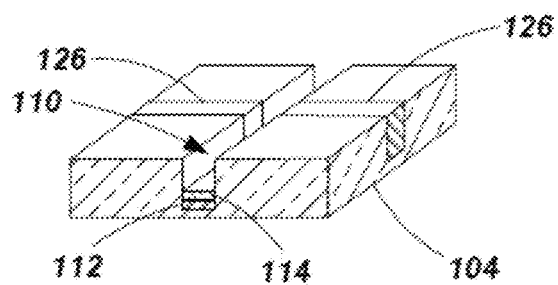

FIGS. 1A-1N illustrate an example method of fabricating a nanochannel DNA sequencing device by depicting a series images shown in a cross-sectional perspective view, as the device is constructed through various stages of fabrication. Referring to FIG. 1A, a first step includes deposition of a thin, hard mask (HM) layer 102 on an insulator substrate 104. The substrate may comprise, for example, SiO2 or glass. A resist layer 106 may, for example, be spin-coated on a top surface of the HM layer 102.

As seen in FIG. 1B, a second step includes patterning a trench 108 in the resist layer 106. The trench 108 may be patterned using any of a various lithography tools, including, for example, deep ultraviolet (DUV) lithography, 193 nm lithography, e-beam lithography, nanoimprint lithography (NIL), and so on. As shown in FIG. 1C, (and as will be discussed in further detail below) the trench is shrunk and smoothed using a thermal re-flow process wherein width of the trench is decreased. This re-flowing process can be repeated until achieving a targeted narrow trench width, for example, in a range of about 10 nm to about 20 nm. Thus, comparing FIGS. 1B and 1C, the trench width is decreased from a width of "a", as shown in FIG. 1B, to a width of "b" as indicated in FIG. 1C.

Referring to FIG. 1D, a pattern transfer into HM layer takes place and then into the substrate using, for example reactive ion etching (RIE) creating a trench 110 in the insulator substrate 104. The HM layer 102 is then stripped as shown in FIG. 1E, and a metal layer 112 is deposited as a capping layer over the substrate 104, including on the floor of the trench 110 as shown in FIG. 1F. It is noted that the metal, or metal materials, in this description may generally refer to a conductor or an electronically conductive material, and may include any desired conductive material.

As seen in FIG. 1G, an etching back step is performed to remove the metal capping layer 112 from the upper surface of the substrate 104, but not from inside the narrow trench. Next, as shown in FIG. 1H, a thin insulator material 114 is disposed within the trench 110, covering the metal layer 112 disposed on the floor of trench 110. A temporary fill material 116 is deposited to fill the trench 110 as shown in FIG. 1I. In one embodiment the deposition of the fill material may be effected by first spin coating the material across the entire device, filling the trench, and then etching back the material to remove it from the upper surface of the substrate 104 while leaving the material in the trench 110. The fill material may include a material that is generally resistant to etching by plasma oxygen processes, but may be removed by a wet etch process or by a dry etch process using a gas other than oxygen. Examples of some materials that may be used as the fill material 116 include, but are not limited to, Cr, Ti, SiN, and SiON.

A second trench, oriented at an angle (e.g., 90°) from the first trench 110 is formed using trench patterning and thermal re-flow processes as illustrated in FIGS. 1J-1N. For example, a resist layer 120 is formed over the substrate 104 and a trench 122 may be patterned in the resist layer 120 as indicated FIG. 1J. The trench 122 may be patterned using any of a various lithography tools such as described above. While not specifically shown, a re-flow process may be used to decrease the width of the trench 122 formed in the resist layer 120 such as previously noted and as will be further detailed below.

The trench pattern is transferred into the substrate, as seen in FIG. 1K, but the process does not etch the fill material 116, forming a new trench 124 in the substrate which is at a desired angle (e.g., 90°) relative to the first trench 110. A metal material may then be deposited into the trench 124 formed within the substrate 104, forming metal lines 126 that will be use in a tunneling current electrode (TCE). Next the resist layer 120 is stripped, and the substrate 104 may be slightly etched back such that the fill material 116 has an open line as shown in FIG. 1M. The fill material 116 is then removed, leaving the trench 110 for use as a DNA nanochannel.

Figure 2A:
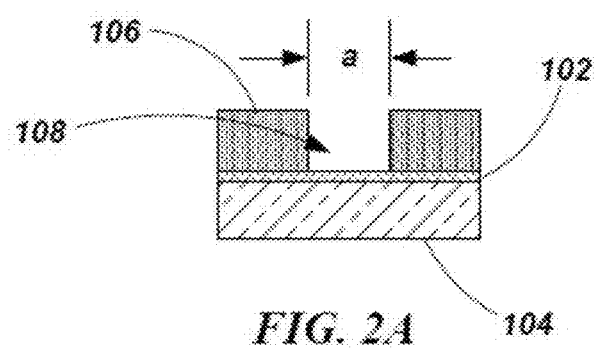
FIGS. 2A-2D illustrate additional fabrication steps for forming a DNA nanochannel device in accordance with an embodiment of the present disclosure.

Referring to FIGS. 2A-2D, a thermal re-flow process, such as used in forming trenches as described above, is illustrated. FIG. 2A shows a cross-sectional side view of a device including an HM layer 102 formed on a substrate 104, and a resist layer 106 disposed over the HM layer 102, the resist layer having a trench 108 formed therein, such as previously described with respect to FIG. 1B. The trench 108 has an initial width of dimension "a" as seen in FIG. 2A.

Figure 2B:
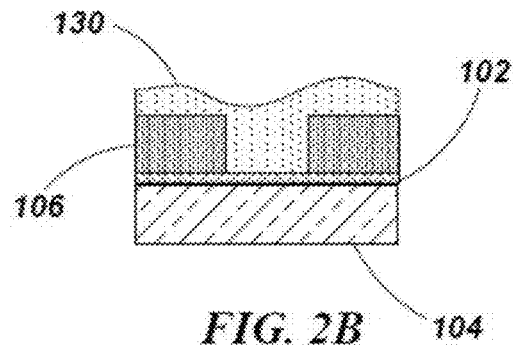
Figure 2C:
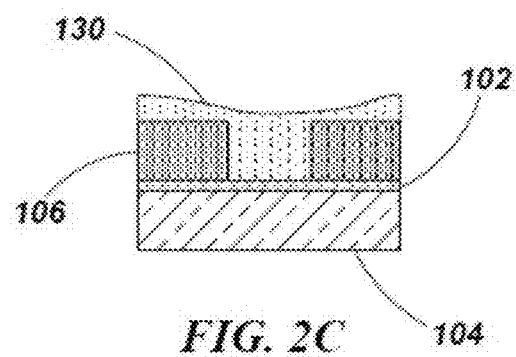
Figure 2D:
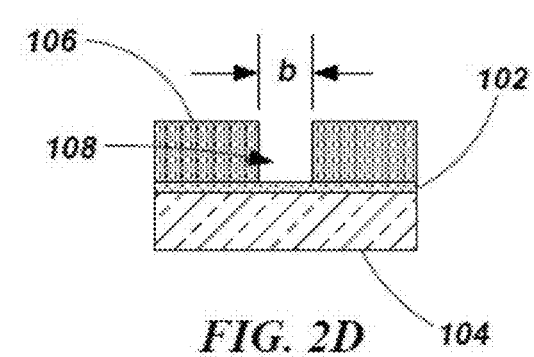

As illustrated in FIG. 2B, a top coat 130 of thermal re-flow material is formed over the resist layer 106 and into trench 108. In one embodiment, the top coat may include a water-based solution with surfactants that have positively and negatively charged functional groups. The positively and negatively charged functional groups may interact with each other indirectly through the water (or other easily polarized medium). As indicated in FIG. 2C, the device is baked (for example, at approximately 100-180° C. for approximately 90 seconds), evaporating the water from the top coat material, enabling the positively and negatively charged functional groups to have direct interactions with each other. The direct interactions of the functional groups cause the top coat material to maintain the profile of the resist material 106 (e.g., the profile of the trench 108) while the top coat material undergoes thermal expansion. This enables the sidewalls of the trench 108 formed in the resist layer to remain vertical in its previously determined pattern, while shrinking the width of the trench 108 by effectively moving the walls of the trench closer to one another. The top coat 130 is removed, the resist material 106 is rinsed with deionized water, and the resulting trench 108 formed in the resist material 106 exhibits a width "b", the dimension "b" being smaller than the dimension "a" as indicated in FIG. 2D.

Figure 3:
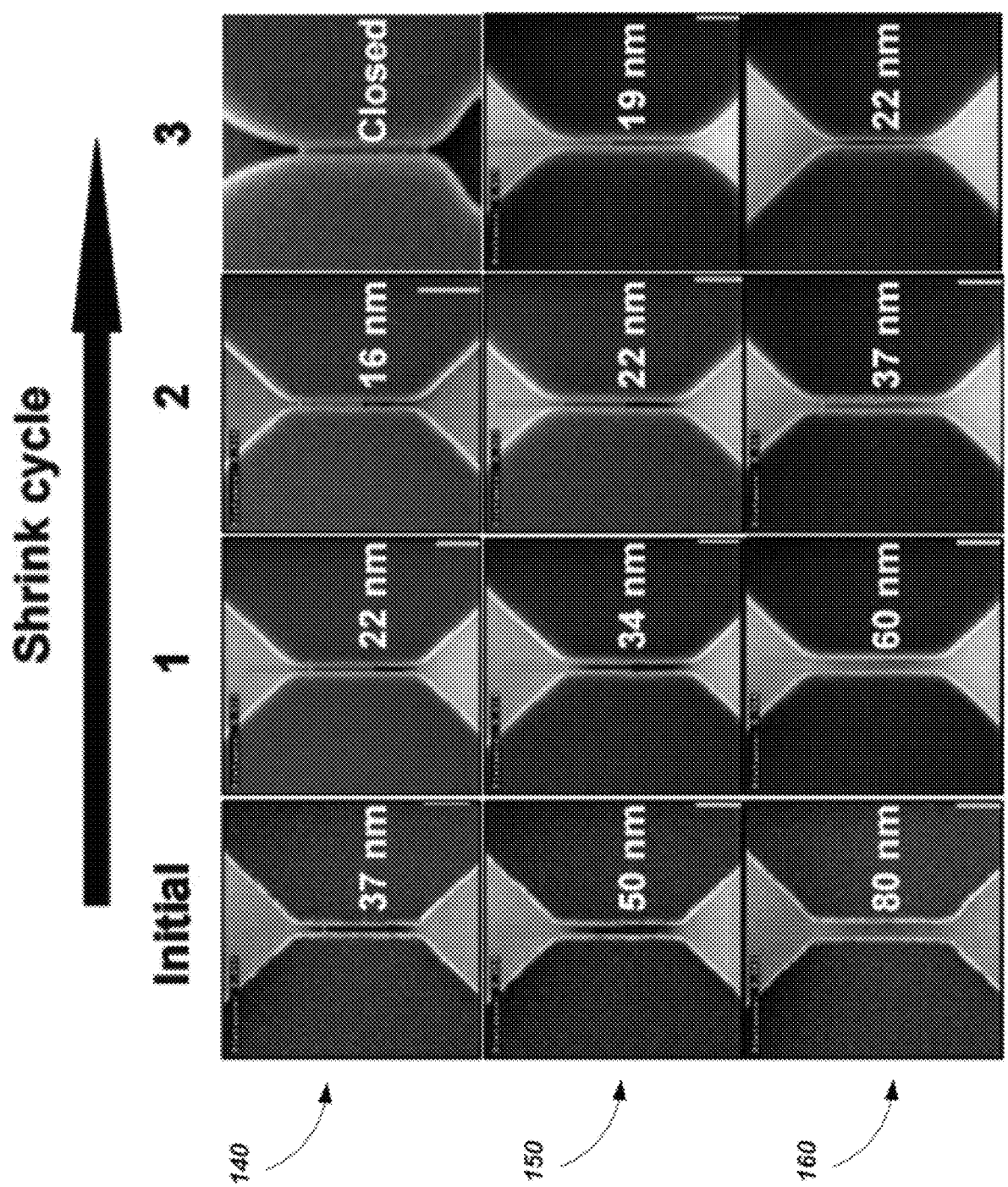
FIG. 3 shows an example shrink cycle using a thermal re-flow process in accordance with the present disclosure.
Figure 4:
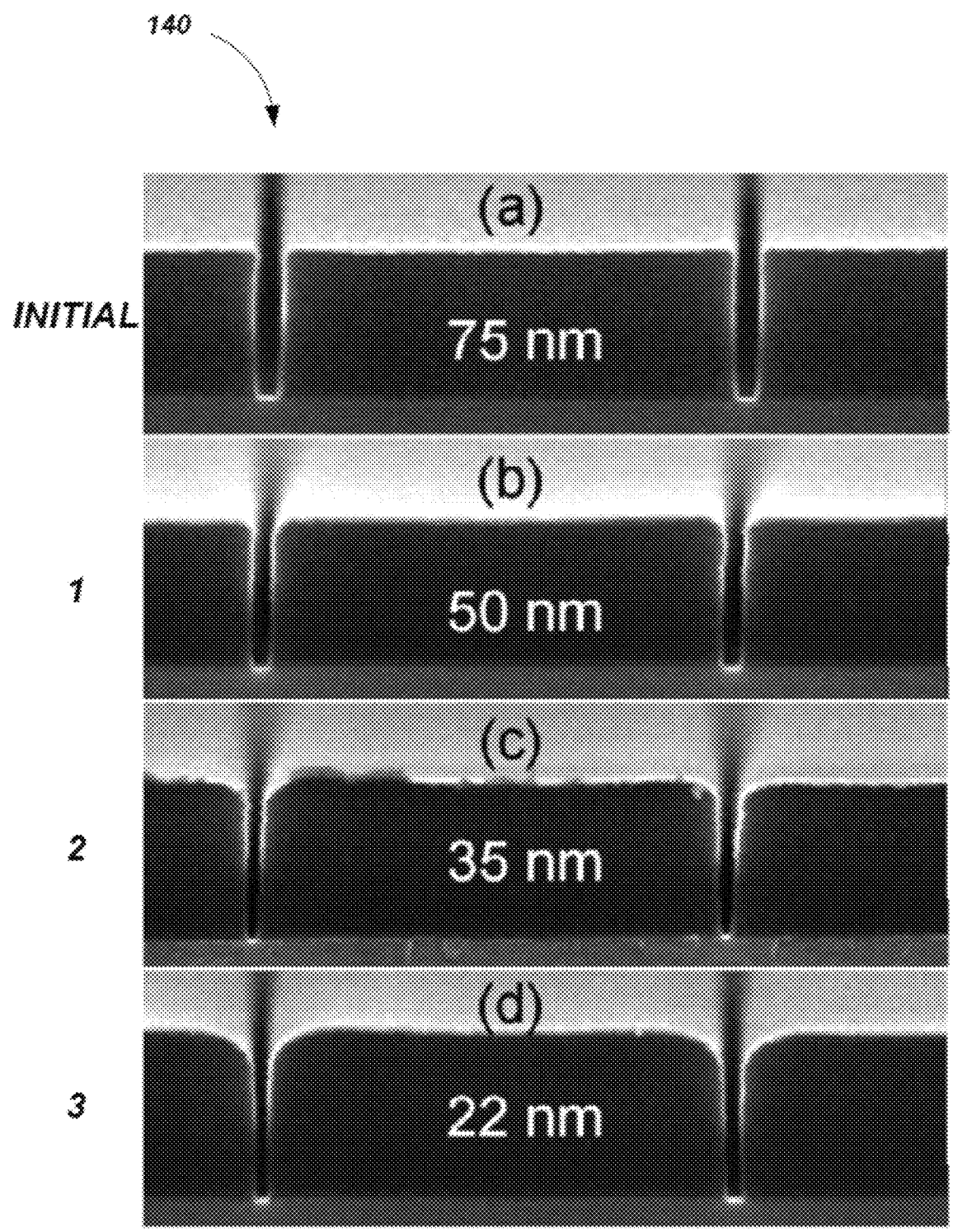
FIG. 4 shows another example shrink cycle using a thermal re-flow process in accordance with the present disclosure.

The thermal re-flow process may be repeated multiple times to further shrink the width of the trench if desired. For example, FIGS. 3 and 4 are microphotographs depicting a trench formed in a device that has undergone multiple thermal re-flow processes such as described above. As seen in FIG. 3, an first specimen 140 starts out with a trench width, or a gap, or 37 nm. After a first thermal re-flow process, or "shrink cycle," the gap is reduced to 22 nm. After a second shrink cycle, the gap is narrowed to 16 nm. A third shrink cycle caused the gap to completely close.

The second specimen 150 shown in FIG. 3 shows an initial gap of 50 nm, a gap of 34 nm after a first shrink cycle, a gap of 22 nm after a second shrink cycle, and a gap of 19 nm after a third shrink cycle.

The third specimen 160 shown in FIG. 3 shows an initial gap of 80 nm, a gap of 60 nm after a first shrink cycle, a gap of 37 nm after a second shrink cycle, and a gap of 22 nm after a third shrink cycle.

Referring to FIG. 4, a profile view of a specimen 170 is shown that has been subjected to multiple shrink cycles or thermal re-flow processes. The specimen 170 shows an initial gap of 75 nm, a gap of 50 nm after a first shrink cycle, a gap of 35 nm after a second shrink cycle, and a gap of 22 nm after a third shrink cycle. It is noted that the sidewalls of the trench remain vertical, providing a trench or channel with a very high aspect ratio (e.g., 1:20 or even greater).

Figure 5:
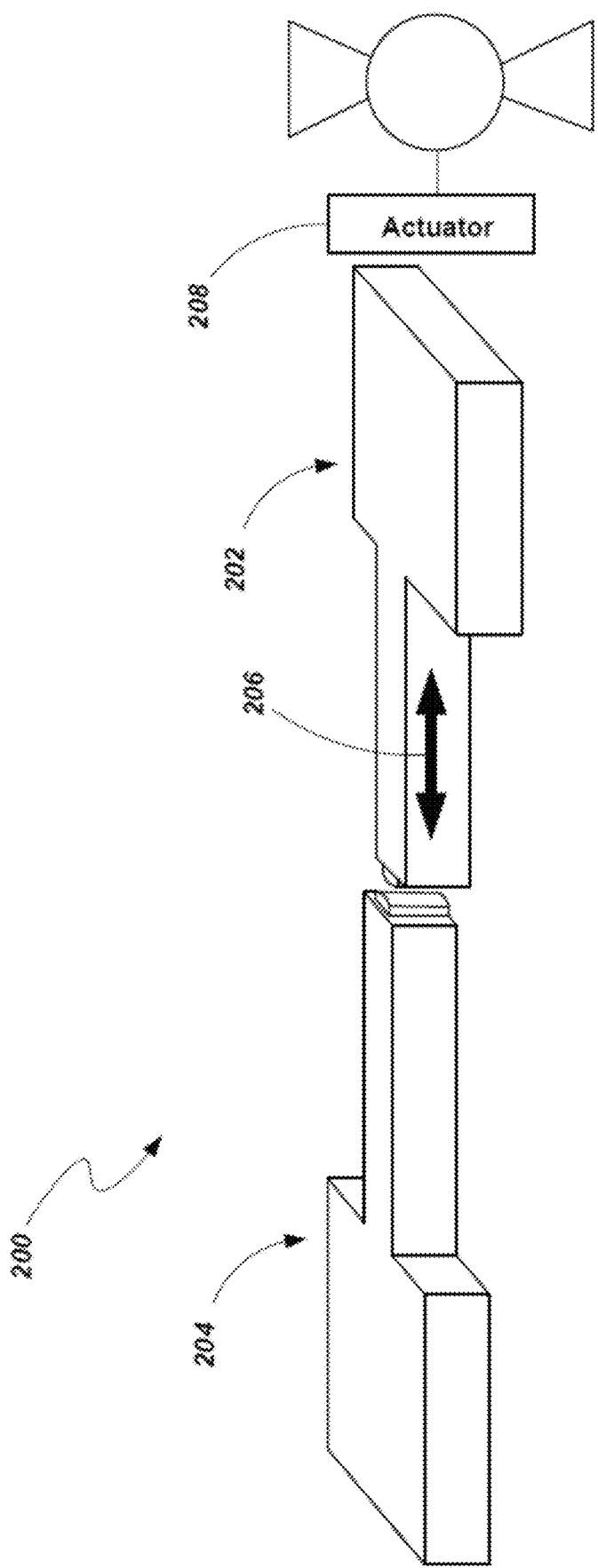
FIG. 5 shows an electrode pair for use in a DNA nanochannel device in accordance with the present disclosure.

In providing a DNA sequencing device, it may be desirable to provide a TCE electrode with a TCE gap of approximately 1 nm or less. In one embodiment that provides such a small TCE gap, at least one of the TCE electrode members may be configured as a suspended electrode. For example, as generally shown in FIG. 5, a TCE electrode 200 may include a first electrode member 202 which may be a "fixed" member, and a second electrode member 204 which is configured as a suspended member and may be laterally displaceable relative to the first electrode member 202 as indicated by directional arrow 206. For example, an actuator 208 may be used to reduce the TCE gap down to a value of less than 1 nm. While shown schematically in FIG. 5, such an actuator 208 may be integrated into the resulting device (e.g., as an "on-chip" actuator), using known nanofabrication techniques as will be appreciated by those of ordinary skill in the art. The formation of a suspended electrode member may be accomplished using techniques discussed above, by deposition of metal onto a suspended pre-defined line structure using known nanofabrication techniques.

Figure 6:
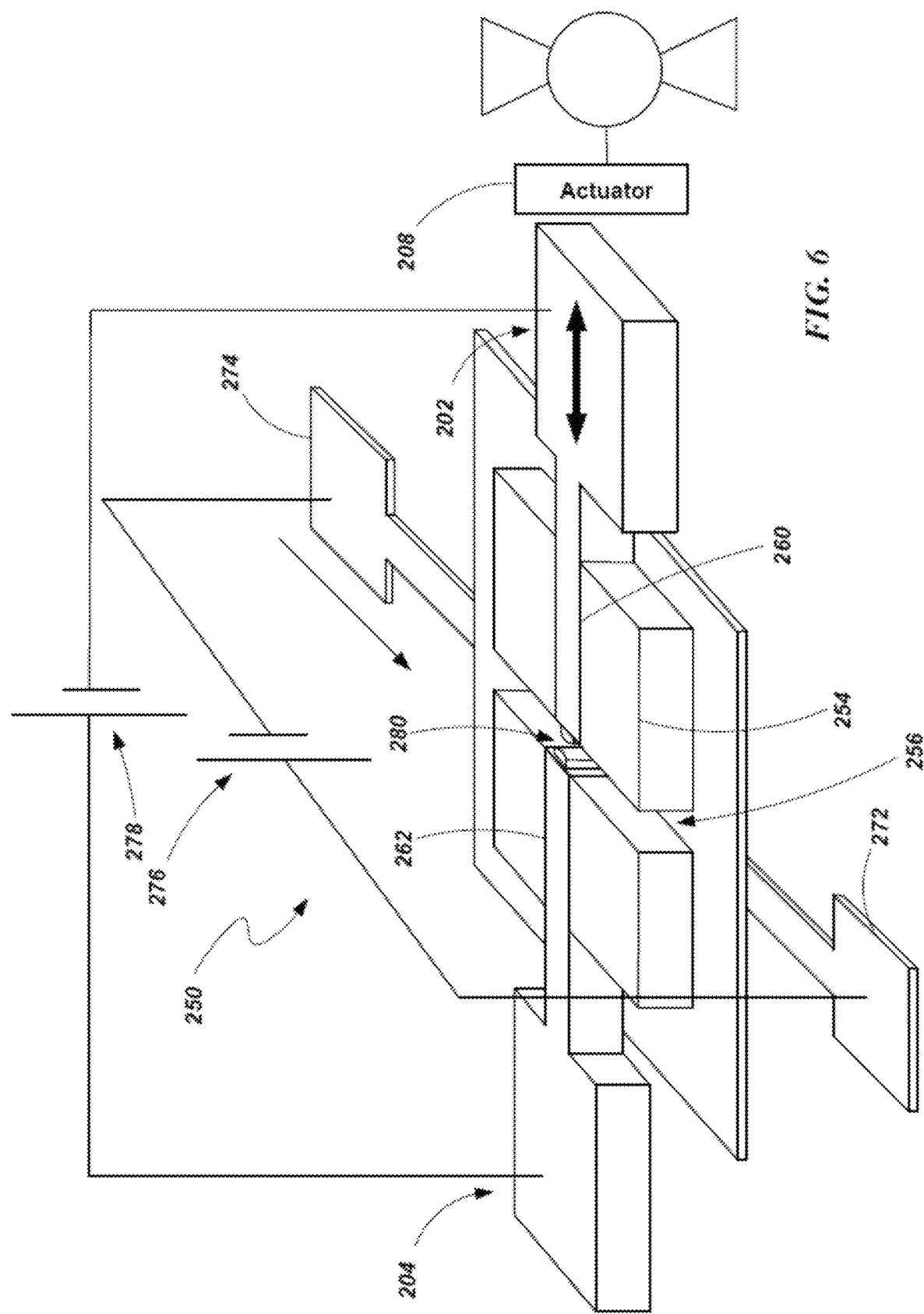
FIG. 6 shows an example DNA nanochannel device in accordance with the present disclosure.
Figure 7:
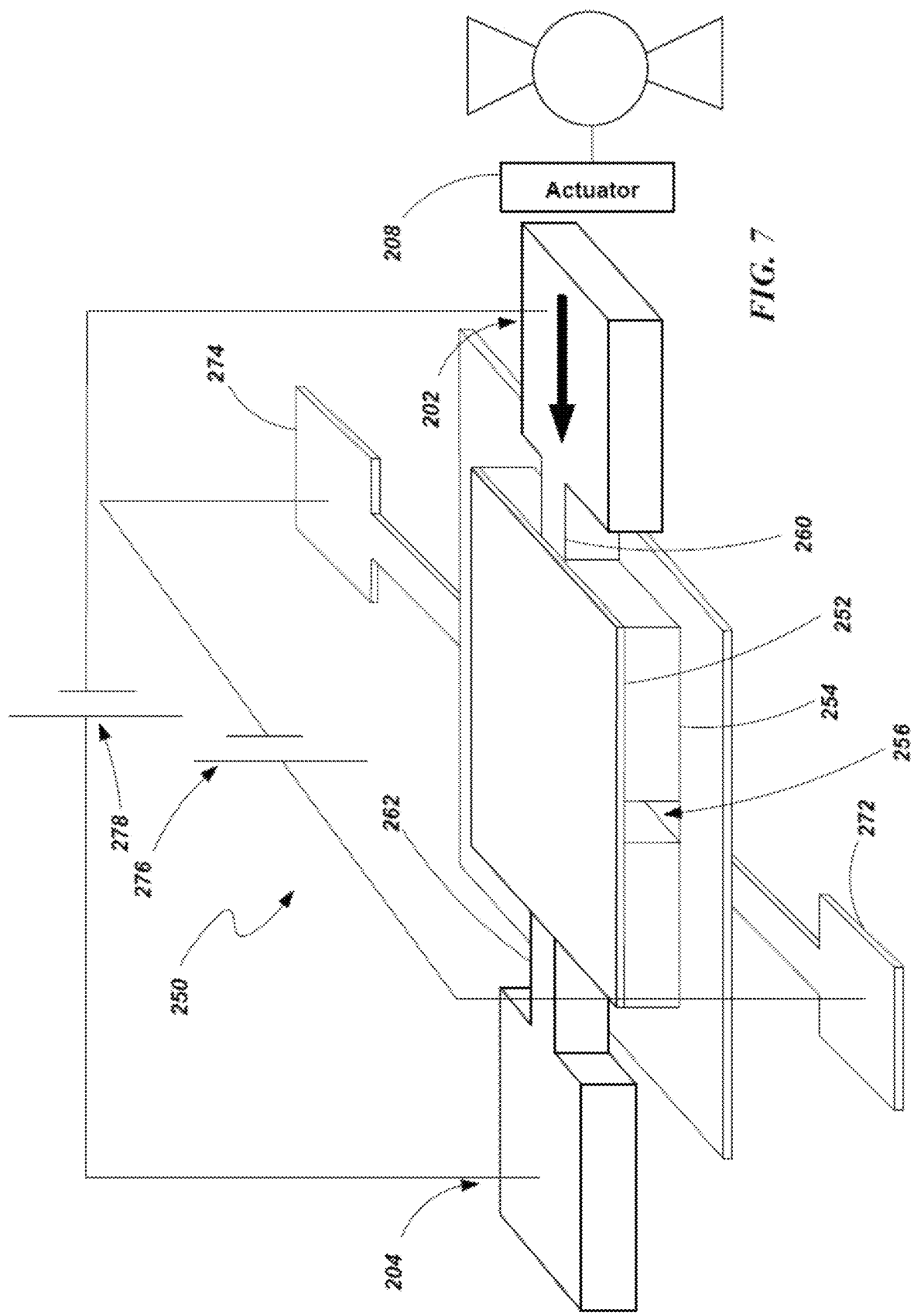
FIG. 7 shows the device of FIG. 4 with a sealing layer disposed atop the electrodes and nanochannel.

Referring to FIGS. 6 and 7, a DNA sequencing device 250 is shown according to one example of the present disclosure. FIG. 7 depicts the device 250 with a top seal 252 in place, while FIG. 6 depicts the device with the top seal removed for purposes of clarity. In one embodiment, the top seal 252 may include polydimethylsiloxane (PDMS). For example, the PDMS material may be mixed with a curing agent at a ratio of 10:1 (by weight), applied to a mold and then baked in an oven at approximately 150° C. for approximately 10 minutes. This produces a rubber film which may be placed on the device (e.g., on a device such as shown in FIG. 1N). The device and rubber film are then both exposed to an oxygen plasma treatment for approximately 1-3 minutes to bond the rubber film to the device and also causing the rubber film to become super-hydrophilic.

Still referring to FIGS. 6 and 7, the device 250 includes an insulating substrate 254 in which is formed a channel 256 through which a single strand of DNA may be passed. The channel may be constructed, for example, similar to, and in accordance with, the devices and processes described hereinabove. In one embodiment, the channel 256 may exhibit a width (between its two sidewalls) of approximately 0.3 nm to approximately 20 nm and, in one particular embodiment, approximately 10 nm to approximately 20 nm. The channel 256 may also exhibit a height of approximately 5 nm to approximately 20 nm and, more particularly, approximately 10 nm to approximately 20 nm.

The device 250 further includes a TCE 200 (such as shown in FIG. 5) having a first electrode member 202 and a second electrode member 204. The first electrode member 202 includes a conductive line 260 extending through a portion of the insulating substrate 254. Likewise, the second electrode member 204 includes a conductive line 262 extending through a portion of the insulating substrate 254. In one embodiment, the conductive lines 260 and 262 of the TCE 200 may exhibit a width of approximately 0.3 nm to approximately 20 nm, and more particularly approximately 10 nm to approximately 20 nm. Additionally, the conductive lines 260 and 262 may exhibit a height of approximately 5 nm to approximately 20 nm and, more particularly, approximately 10 nm to approximately 20 nm. The electrode members 202 and 204 may be constructed, for example, similar to, and in accordance with, the devices and processes described hereinabove.

The first and second electrode members 202 and 204 may each include a refined tip (e.g., pointed or exhibiting a desired radius) positioned at a desired distance relative to each other. In one embodiment, an actuator 208 may be associated with the second electrode member 204, which may be configured as a suspended electrode, such that it may be displaced relative to the first electrode member 202, changing the gap distance between the two electrode members 202 and 204. In another embodiment, each of the electrode members 202 and 204 may be configured as suspended electrodes and have actuators associated therewith such that each electrode member 202 and 204 is independently displaceable relative to the other. In one embodiment, the TCE electrode is configured to exhibit a gap between the two electrode members 202 and 204 (i.e., the "TCE gap" of approximately 0.1 nm to approximately 2 nm, and more particularly approximately 0.3 nm to approximately 1 nm.

The device 250 further includes a second pair of electrode members 272 and 274 associated with the DNA channel 256. A first voltage 276 may be applied across the second pair of electrode members 272 and 274 to act as a motive force in drawing a DNA strand through the channel 256 and past the TCE electrode gap 280. A second voltage 278 may be applied to the TCE electrode 200 to read the signal of a DNA strand as it passes through the TCE gap formed in the channel 256.

Figure 8:
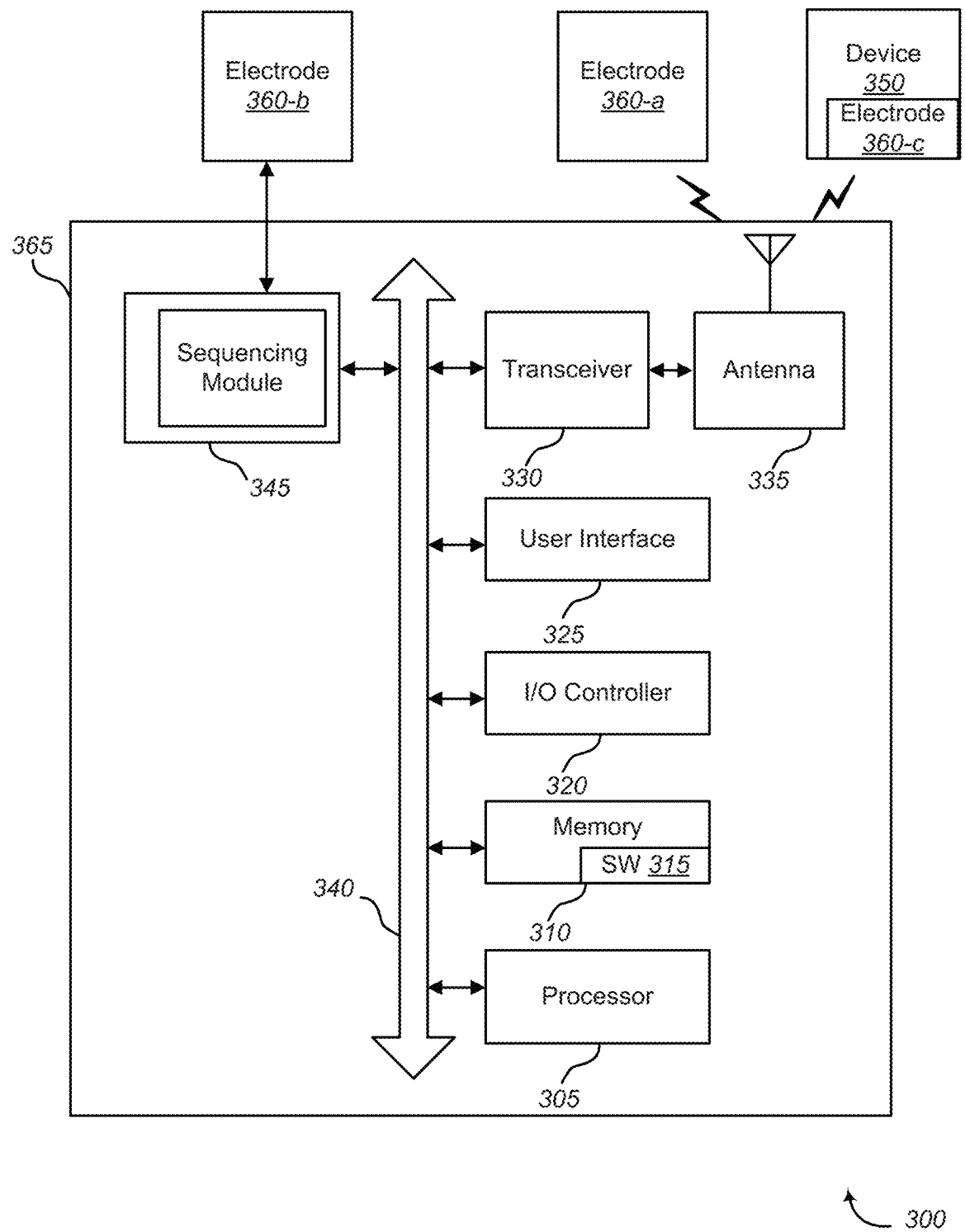
FIG. 8 shows a diagram of a system in accordance with various aspects of this disclosure.

FIG. 8 shows a system 300 for use with the DNA sequencing devices and systems shown in FIGS. 1-7. System 300 may include a control panel 365. Control panel 365 may be equivalent at least in part to a controller, control unit, processor or the like for use with the devices described above with reference to FIGS. 1-3. Control panel 365 may include sequencing module 345. The sequencing module 345 may provide communications with one or more electrodes 360 (also referred to as sensors or devices) directly or via other communication components, such as a transceiver 330 and/or antenna 335. The electrodes 360 may represent one or more of the electrodes 126, 206, or pairs of such electrodes in any of the embodiments described above. The sequencing module 345 may perform or control various operations associated with, for example, the electrodes 126, 206, actuator 208, controller, or other components of the DNA sequencing devices and related systems as described above with reference to FIGS. 1-7.

Control panel 365 may also include a processor module 305, and memory 310 (including software/firmware code (SW) 315), an input/output controller module 320, a user interface module 325, a transceiver module 330, and one or more antennas 335 each of which may communicate, directly or indirectly, with one another (e.g., via one or more buses 340). The transceiver module 330 may communicate bi-directionally, via the one or more antennas 335, wired links, and/or wireless links, with one or more networks or remote devices. For example, the transceiver module 330 may communicate bi-directionally with one or more of device 350 and/or electrodes 360-a, 360-c. The device 350 may be components of the DNA sequencing devices and related systems and devices described with reference to FIGS. 1-7, or other devices in communication with such systems and devices. The transceiver 330 may include a modem to modulate the packets and provide the modulated packets to the one or more antennas 335 for transmission, and to demodulate packets received from the one or more antennas 335. In some embodiments (not shown) the transceiver may be communicate bi-directionally with one or more of device 350, remote control device 355, and/or electrodes 360-a, 360-c through a hardwired connection without necessarily using antenna 335. While a control panel or a control device (e.g., 305) may include a single antenna 335, the control panel or the control device may also have multiple antennas 335 capable of concurrently transmitting or receiving multiple wired and/or wireless transmissions. In some embodiments, one element of control panel 365 (e.g., one or more antennas 335, transceiver module 330, etc.) may provide a connection using wireless techniques, including digital cellular telephone connection, Cellular Digital Packet Data (CDPD) connection, digital satellite data connection, and/or another connection.

The signals associated with system 300 may include wireless communication signals such as radio frequency, electromagnetics, local area network (LAN), wide area network (WAN), virtual private network (VPN), wireless network (using 302.11, for example), 345 MHz, Z-WAVE®, cellular network (using 3G and/or LTE, for example), and/or other signals. The one or more antennas 335 and/or transceiver module 330 may include or be related to, but are not limited to, WWAN (GSM, CDMA, and WCDMA), WLAN (including BLUETOOTH® and Wi-Fi), WMAN (WiMAX), antennas for mobile communications, antennas for Wireless Personal Area Network (WPAN) applications (including RFID and UWB). In some embodiments, each antenna 335 may receive signals or information specific and/or exclusive to itself. In other embodiments, each antenna 335 may receive signals or information not specific or exclusive to itself.

In some embodiments, one or more electrodes 360 (e.g., voltage, inductance, resistance, current, force, temperature, etc.) or devices 350 may connect to some element of system 300 via a network using one or more wired and/or wireless connections. In some embodiments, the user interface module 325 may include an audio device, such as an external speaker system, an external display device such as a display screen, and/or an input device (e.g., remote control device interfaced with the user interface module 325 directly and/or through I/O controller module 320).

One or more buses 340 may allow data communication between one or more elements of control panel 365 (e.g., processor module 305, memory 310, I/O controller module 320, user interface module 325, etc.).

The memory 310 may include random access memory (RAM), read only memory (ROM), flash RAM, and/or other types. The memory 310 may store computer-readable, computer-executable software/firmware code 315 including instructions that, when executed, cause the processor module 305 to perform various functions described in this disclosure (e.g., initiating an adjustment of a lighting system, etc.). Alternatively, the software/firmware code 315 may not be directly executable by the processor module 305 but may cause a computer (e.g., when compiled and executed) to perform functions described herein. Alternatively, the computer-readable, computer-executable software/firmware code 315 may not be directly executable by the processor module 305 but may be configured to cause a computer (e.g., when compiled and executed) to perform functions described herein. The processor module 305 may include an intelligent hardware device, e.g., a central processing unit (CPU), a microcontroller, an application-specific integrated circuit (ASIC), etc.

In some embodiments, the memory 310 can contain, among other things, the Basic Input-Output system (BIOS) which may control basic hardware and/or software operation such as the interaction with peripheral components or devices. For example, the sequencing module 345, and other modules and operational components of the control panel 365 used to implement the present systems and methods may be stored within the system memory 310. Applications resident with system 300 are generally stored on and accessed via a non-transitory computer readable medium, such as a hard disk drive or other storage medium. Additionally, applications can be in the form of electronic signals modulated in accordance with the application and data communication technology when accessed via a network interface (e.g., transceiver module 330, one or more antennas 335, etc.).

Many other devices and/or subsystems may be connected to one or may be included as one or more elements of system 300. In some embodiments, all of the elements shown in FIG. 8 need not be present to practice the present systems and methods. The devices and subsystems can be interconnected in different ways from that shown in FIG. 8. In some embodiments, an aspect of some operation of a system, such as that shown in FIG. 8, may be readily known in the art and are not discussed in detail in this application. Code to implement the present disclosure can be stored in a non-transitory computer-readable medium such as one or more of system memory 310 or other memory. The operating system provided on I/O controller module 320 may be iOS®, ANDROID®, MS-DOS®, MS-WINDOWS®, OS/2®, UNIX®, LINUX®, or another known operating system.

The transceiver module 330 may include a modem configured to modulate the packets and provide the modulated packets to the antennas 335 for transmission and/or to demodulate packets received from the antennas 335. While the control panel or control device (e.g., 305) may include a single antenna 335, the control panel or control device (e.g., 305) may have multiple antennas 335 capable of concurrently transmitting and/or receiving multiple wireless transmissions.

Figure 9:
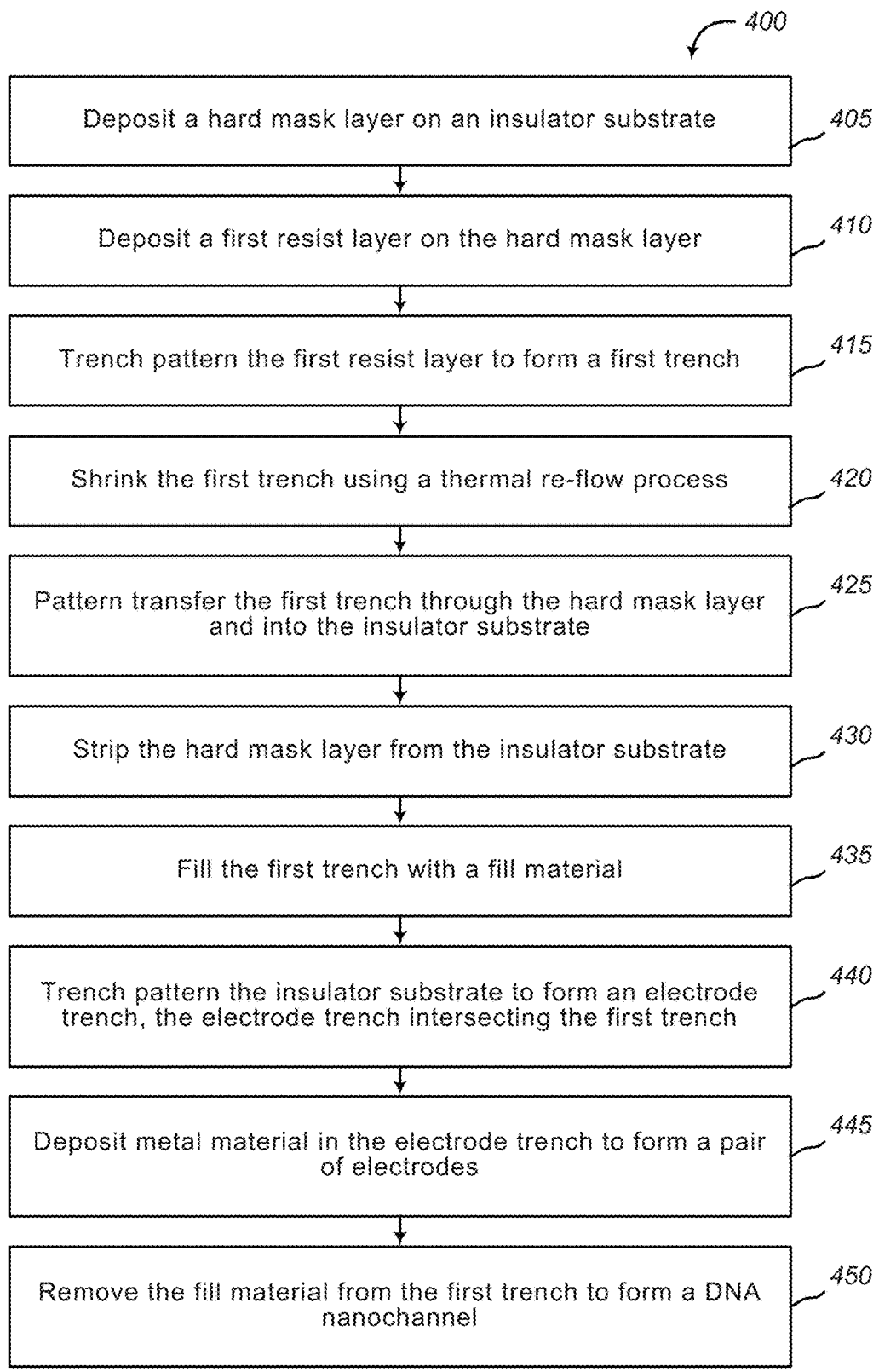
FIG. 9 is a flow diagram showing steps of an example method in accordance with the present disclosure.
Figure 10:
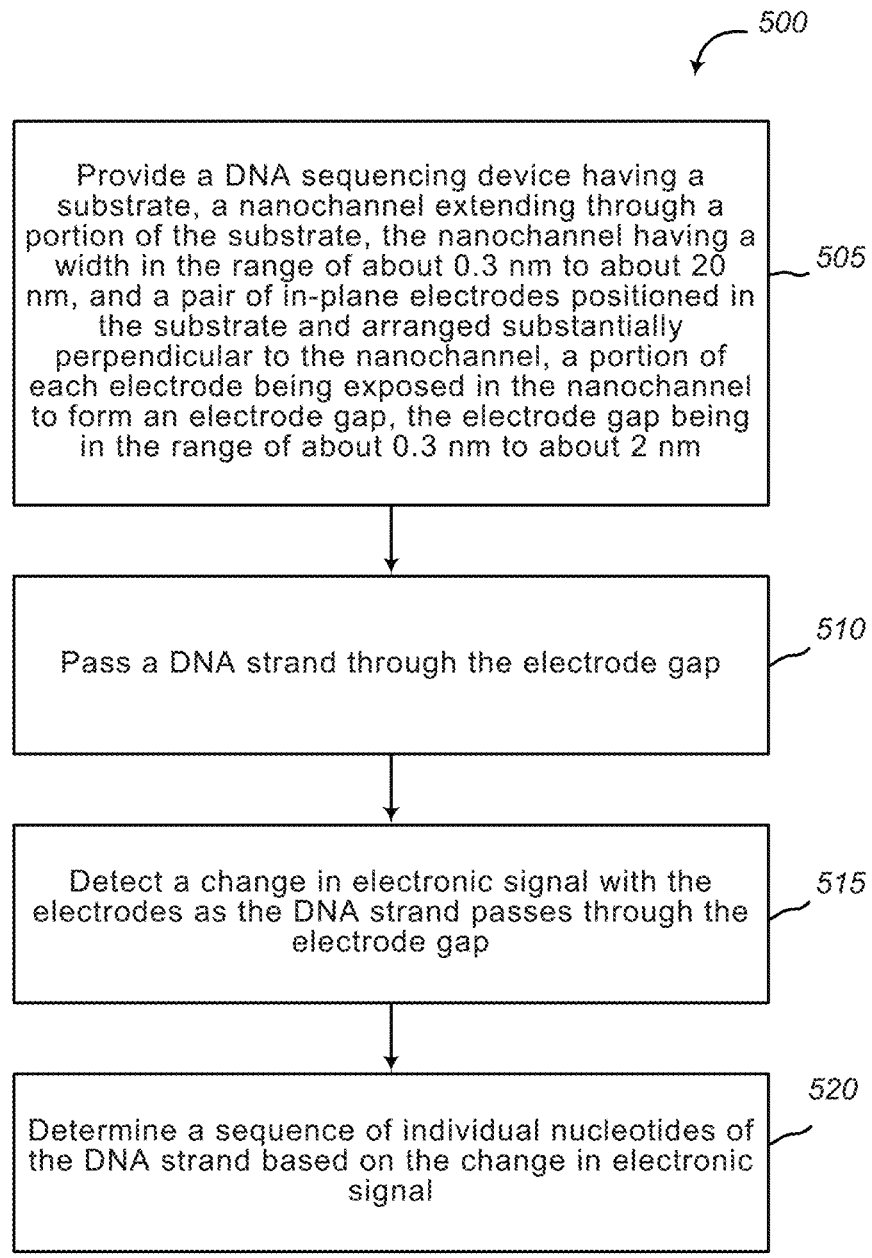
FIG. 10 is a flow diagram showing steps of another example method in accordance with the present disclosure.

FIGS. 9 and 10 are flow diagrams illustrating example methods associated with the DNA sequencing devices disclosed herein. FIG. 9 illustrates a method 400 method of forming a nanochannel device for DNA sequencing. At block 405, the method 400 includes depositing a hard mask layer on an insulator substrate. Block 410 includes depositing a first resist layer on the hard mask layer. Block 415 includes trench patterning the first resist layer to form a first trench. Block 420 includes shrinking the first trench using a thermal re-flow process. Block 425 includes pattern transferring the first trench through the hard mask layer and into the insulator substrate. Block 430 includes stripping the hard mask layer from the insulator substrate. Block 435 includes filling the first trench with a fill material. Block 440 includes trench patterning the insulator substrate to form an electrode trench, the electrode trench intersecting the first trench. Block 445 includes depositing metal material in the electrode trench to form a pair of electrodes. Block 450 includes removing the fill material from the first trench to form a DNA nanochannel.

The method 400 may also include trench patterning using at least one of deep ultraviolet (DUV) lithography, 193 nm lithography, e-beam lithography, and nanoimprint lithography (NIL). The method 400 may include repeating the step of shrinking the first trench until the first trench has a first trench width in the range of about 0.3 nm to about 20 nm. Shrinking the first trench using a thermal re-flow process may include disposing a top coat over at least a portion of the substrate and within the first trench, baking the device with the top coat at a temperature of approximately 100° C. to approximately 180° C. for approximately 60 seconds to approximately 90 seconds, and removing the top coat from the substrate and the first trench. The method 400 may include, after stripping the hard mask layer, depositing a metal layer on the insulator substrate as a capping layer, the metal layer positioned along a bottom surface of the first trench, etching to remove the metal layer from the insulator substrate except in the first trench, and depositing an insulator material in the first trench to cover the metal layer deposited in the first trench. Filling the first trench with the filler material may include spin coating the filler material on the insulator substrate and in the first trench, and etching back the filler material from the insulator substrate except within the first trench.

The method 400 may include, after filling the first trench with the filler material, depositing a second resist layer on the insulator substrate, trench patterning the second resist layer to form a second trench, shrinking the second trench using the thermal re-flow process, and trench patterning the insulator substrate to form the electrode trench using the second trench as a pattern. The method 400 may include, after depositing metal material in the electrode trench, etching back the metal material to expose the fill material. The electrodes may be spaced apart to form an electrode gap, the electrode gap positioned in the nanochannel and exhibiting a width in the range of about 0.3 nm to about 2 nm. The method 400 may include forming at least a first electrode of the electrode pair as a suspended electrode and coupling the first electrode with an actuator to displace the first electrode relative to a second electrode of the electrode pair to vary the width of the electrode gap. A width of nanochannel may be in the range of about 0.3 nm to about 20 nm, and a height of the nanochannel may be in the range of about 5 nm to about 20 nm, and the electrode may have a width in the range of about 0.1 nm to about 20 nm, and a height in the range of about 5 nm to about 20 nm.

FIG. 10 illustrates a method 500 of DNA sequencing. The method 500 may include, at block 505, providing a DNA sequencing device having a substrate, a nanochannel extending through a portion of the substrate, the nanochannel having a width in the range of about 0.3 nm to about 20 nm, and a pair of in-plane electrodes positioned in the substrate and arranged substantially perpendicular to the nanochannel, a portion of each electrode being exposed in the nanochannel to form an electrode gap, the electrode gap being in the range of about 0.3 nm to about 2 nm. The method 500 further includes passing a DNA strand through the electrode gap, detecting a change in electronic signal with the electrodes as the DNA strand passes through the electrode gap, and determining a sequence of individual nucleotides of the DNA strand based on the change in electronic signal.

The example methods 400, 500 may, in other embodiments, include fewer or additional steps that those illustrated in FIGS. 9 and 10. Further, many other methods and method steps may be possible based on the disclosures provided herein.

In some embodiments, the DNA sequencing device and systems described herein may be used to collect electronic signals associated with the nucleotides of a DNA strand passing through the gap between electrode pairs, and the collected electronic signals are processed at a different location. The processing may include electronically comparing the collected electronic signals to ranges of electronic signals associated with specific nucleotide types which have been previously determined and stored. In other embodiments, the DNA sequencing device includes capability of processing the collected electronic signals, conducting such comparison evaluations, and even formulating an order or sequence for the nucleotides of the DNA strand being evaluated.

INCORPORATION BY REFERENCE

The entire content of each of the previously filed provisional patent applications listed below are incorporated by reference in their entireties into this document, as are the related non-provisional patent applications of the same title filed concurrently with the present application. If the same term is used in both this document and one or more of the incorporated documents, then it should be interpreted to have the broadest meaning imparted by any one or combination of these sources unless the term has been explicitly defined to have a different meaning in this document. If there is an inconsistency between any of the following documents and this document, then this document shall govern. The incorporated subject matter should not be used to limit or narrow the scope of the explicitly recited or depicted subject matter.

U.S. Prov. App. No. 62/453,270, titled "SINGLE-MOLECULE DNA SEQUENCING METHOD USING CONFINED NANO-FLUIDIC CHANNEL AND SUB-NANOMETER ELECTRODE GAP," filed on 1 Feb. 2017, and U.S. patent application Ser. No. 15/886,442, titled "SINGLE-MOLECULE DNA SEQUENCING METHOD USING CONFINED NANO-FLUIDIC CHANNEL AND SUB-NANOMETER ELECTRODE GAP," filed on 1 Feb. 2018.

U.S. Prov. App. No. 62/453,398, titled "NANOFLUIDIC CHANNEL OPENING SIZE CONTROL USING ACTUATION," filed on 1 Feb. 2017, and U.S. patent application Ser. No. 15/886,483, titled "NANOFLUIDIC CHANNEL OPENING SIZE CONTROL USING ACTUATION," filed on 1 Feb. 2018.

U.S. Prov. App. No. 62/453,298, titled "FABRICATION OF NANOCHANNEL WITH INTEGRATED ELECTRODES FOR DNA SEQUENCING USING TUNNELING CURRENT," filed on 1 Feb. 2017, and U.S. patent application Ser. No. 15/886,511, titled "FABRICATION OF NANOCHANNEL WITH INTEGRATED ELECTRODES FOR DNA SEQUENCING USING TUNNELING CURRENT," filed on 1 Feb. 2018.

U.S. Prov. App. No. 62/453,323, titled "FABRICATION OF A DEVICE FOR SINGLE-MOLECULE DNA SEQUENCING USING SIDEWALL LITHOGRAPHY," filed on 1 Feb. 2017, and U.S. patent application Ser. No. 15/886,560 titled "FABRICATION OF A DEVICE FOR SINGLE-MOLECULE DNA SEQUENCING USING SIDEWALL LITHOGRAPHY," filed on 1 Feb. 2018.

U.S. Prov. App. No. 62/453,339, titled "FABRICATION OF A NANOCHANNEL FOR DNA SEQUENCING USING ELECTRICAL PLATING TO ACHIEVE TUNNELING ELECTRODE GAP," filed on 1 Feb. 2017, and U.S. patent application Ser. No. 15/886,581, titled "FABRICATION OF A NANOCHANNEL FOR DNA SEQUENCING USING ELECTRICAL PLATING TO ACHIEVE TUNNELING ELECTRODE GAP," filed on 1 Feb. 2018.

U.S. Prov. App. No. 62/453,346, titled "NANOSTRUCTURES TO CONTROL DNA STRAND ORIENTATION AND POSITION LOCATION FOR TRANSVERSE DNA SEQUENCING," filed on 1 Feb. 2017, and U.S. patent application Ser. No. 15/886,608, titled "NANOSTRUCTURES TO CONTROL DNA STRAND ORIENTATION AND POSITION LOCATION FOR TRANSVERSE DNA SEQUENCING," filed on 1 Feb. 2018.

U.S. Prov. App. No. 62/453,365, titled "FABRICATION OF WEDGE SHAPED ELECTRODE FOR ENHANCED DNA SEQUENCING USING TUNNELING CURRENT," filed on 1 Feb. 2017, and U.S. patent application Ser. No. 15/886,661, titled "FABRICATION OF WEDGE SHAPED ELECTRODE FOR ENHANCED DNA SEQUENCING USING TUNNELING CURRENT," filed on 1 Feb. 2018.

U.S. Prov. App. No. 62/453,329, titled "DIRECT SEQUENCING DEVICE WITH A TOP-BOTTOM ELECTRODE PAIR," filed on 1 Feb. 2017, and U.S. patent application Ser. No. 15/886,685, titled "DIRECT SEQUENCING DEVICE WITH A TOP-BOTTOM ELECTRODE PAIR," filed on 1 Feb. 2018.

U.S. Prov. App. No. 62/453,376, titled "MICRO AND NANOFLUIDIC CHANNEL CONTROLLED ACTUATION TO OPEN CHANNEL GAP," filed on 1 Feb. 2017.

U.S. Prov. App. No. 62/469,393, titled "METHOD TO AMPLIFY TRANSVERSE TUNNELING CURRENT DISCRIMINATION OF DNA NUCLEOTIDES VIA NUCLEOTIDE SITE SPECIFIC ATTACHMENT OF DYE-PEPTIDE," filed on 9 Mar. 2017, and U.S. patent application Ser. No. 15/886,736, titled "METHOD TO AMPLIFY TRANSVERSE TUNNELING CURRENT DISCRIMINATION OF DNA NUCLEOTIDES VIA NUCLEOTIDE SITE SPECIFIC ATTACHMENT OF DYE-PEPTIDE," filed on 9 Mar. 2018.

U.S. Prov. App. No. 62/469,409, titled "VERTICAL NANOPORE COUPLED WITH A PAIR OF TRANSVERSE ELECTRODES HAVING A UNIFORM ULTRASMALL NANOGAP FOR DNA SEQUENCING," filed on 9 Mar. 2017, and U.S. patent application Ser. No. 15/886,723, titled "VERTICAL NANOPORE COUPLED WITH A PAIR OF TRANSVERSE ELECTRODES HAVING A UNIFORM ULTRASMALL NANOGAP FOR DNA SEQUENCING," filed on 9 Mar. 2018.

The detailed description set forth above in connection with the appended drawings describes examples and does not represent the only instances that may be implemented or that are within the scope of the claims. The terms "example" and "exemplary," when used in this description, mean "serving as an example, instance, or illustration," and not "preferred" or "advantageous over other examples." The detailed description includes specific details for the purpose of providing an understanding of the described techniques. These techniques, however, may be practiced without these specific details. In some instances, known structures and apparatuses are shown in block diagram form in order to avoid obscuring the concepts of the described examples.

In addition, any disclosure of components contained within other components or separate from other components should be considered exemplary because multiple other architectures may potentially be implemented to achieve the same functionality, including incorporating all, most, and/or some elements as part of one or more unitary structures and/or separate structures.

The previous description of the disclosure is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not to be limited to the examples and designs described herein but is to be accorded the broadest scope consistent with the principles and novel features disclosed.

The process parameters, actions, and steps described and/or illustrated in this disclosure are given by way of example only and can be varied as desired. For example, while the steps illustrated and/or described may be shown or discussed in a particular order, these steps do not necessarily need to be performed in the order illustrated or discussed. The various exemplary methods described and/or illustrated here may also omit one or more of the steps described or illustrated here or include additional steps in addition to those disclosed.

This description, for purposes of explanation, has been described with reference to specific embodiments. The illustrative discussions above, however, are not intended to be exhaustive or limit the present systems and methods to the precise forms discussed. Many modifications and variations are possible in view of the above teachings. The embodiments were chosen and described in order to explain the principles of the present systems and methods and their practical applications, to enable others skilled in the art to utilize the present systems, apparatus, and methods and various embodiments with various modifications as may be suited to the particular use contemplated.

What is claimed is:

1. A DNA sequencing device, comprising:
    a substrate;
    a nanochannel extending through a portion of the substrate, the nanochannel having a width in the range of about 0.3 nm to about 20 nm;
    a pair of in-plane electrodes positioned in the substrate and arranged substantially perpendicular to the nanochannel, a portion of each electrode being exposed in the nanochannel to form an electrode gap, the electrode gap being in the range of about 0.3 nm to about 2 nm, wherein at least one of the pair of in-plane electrodes is a suspended electrode coupled with an actuator.

2. The device of claim 1, wherein a height of the nanochannel is in the range of about 5 nm to about 20 nm.

3. The device of claim 1, wherein the electrodes have a width in the range of about 0.1 nm to about 20 nm.

4. The device of claim 1, wherein the electrodes have a height in the range of about 5 nm to about 20 nm.

5. The device of claim 1, wherein the substrate is an insulator substrate.

6. The device of claim 1, further comprising a metal layer disposed along a bottom surface of the channel and an insulator material disposed over the metal layer.

7. The device of claim 1, wherein the substrate comprises SiO2 or glass.

8. The device of claim 1, wherein the actuator configured to displace the first electrode relative to a second electrode of the pair of electrodes.

9. A DNA sequencing device, comprising:
    an insulator substrate;
    a nanochannel extending through a portion of the insulator substrate, the nanochannel having a width in the range of about 0.3 nm to about 20 nm, wherein the nanochannel comprises a metal layer disposed along a bottom surface of the nanochannel and an insulator material disposed over the metal layer;
    a pair of in-plane electrodes positioned in the insulator substrate and arranged substantially perpendicular to the nanochannel, a portion of each electrode being exposed in the nanochannel to form an electrode gap, the electrode gap being in the range of about 0.3 nm to about 2 nm, wherein at least one of the pair of in-plane electrodes is a suspended electrode coupled with an actuator.

10. The device of claim 9, wherein a height of the nanochannel is in the range of about 5 nm to about 20 nm.

11. The device of claim 9, wherein the electrodes have a width in the range of about 0.1 nm to about 20 nm.

12. The device of claim 9, wherein the electrodes have a height in the range of about 5 nm to about 20 nm.

13. The device of claim 9, wherein the substrate comprises SiO2 or glass.

14. The device of claim 9, wherein the actuator configured to displace the first electrode relative to a second electrode of the pair of electrodes.

15. The device of claim 8, wherein the actuator is a shear actuator.

16. The device of claim 8, wherein the actuator is an on-chip actuator.

17. The device of claim 8, wherein each of the in-plane electrodes are suspended electrodes and one of the in-plane electrodes is associated with an actuator.

18. The device of claim 14, wherein the actuator is a shear actuator.

19. A DNA sequencing device, comprising:
a substrate;
a nanochannel extending through a portion of the substrate, the nanochannel having a width in the range of about 0.3 nm to about 20 nm;
a pair of in-plane electrodes positioned in the substrate and arranged substantially perpendicular to the nanochannel, a portion of each electrode being exposed in the nanochannel to form an electrode gap, the electrode gap being in the range of about 0.3 nm to about 2 nm, wherein one of the pair of in-plane electrodes is a suspended electrode coupled with a shear actuator configured to displace the one of the in-plane electrodes relative to another of in-plane electrodes.

* * * * *